United States Patent [19]

Shinohara et al.

[11] 4,265,930

[45] May 5, 1981

[54] PROCESS FOR PRODUCING OXYGEN SENSING ELEMENT

[75] Inventors: Hiroshi Shinohara, Okazaki; Yasuhiro Otsuka, Toyota; Shinichi Matsumoto, Toyota; Toshinobu Furutani, Toyota; Hiroshi Wakizaka, Toyota, all of Japan

[73] Assignee: Toyota Jidosha Kogyo Kabushiki Kaisha, Toyota, Japan

[21] Appl. No.: 50,057

[22] Filed: Jun. 19, 1979

[30] Foreign Application Priority Data

Oct. 23, 1978 [JP] Japan .................. 53/129446

[51] Int. Cl.³ ..................... B05D 1/08; B05D 5/12
[52] U.S. Cl. ..................... 427/34; 204/195 S; 219/121 P
[58] Field of Search ............... 427/34, 423; 204/195 S; 219/121 P

[56] References Cited

U.S. PATENT DOCUMENTS

| | | |
|---|---|---|
| 3,645,875 | 2/1972 | Record et al. ............... 204/195 S |
| 4,021,326 | 5/1977 | Pollner et al. ............... 204/195 S |
| 4,097,353 | 6/1978 | Kishida et al. ............... 427/34 |

OTHER PUBLICATIONS

Davis "Metal Progress" Mar. 1963, pp. 105-108.

Primary Examiner—John H. Newsome
Attorney, Agent, or Firm—Kenyon & Kenyon

[57] ABSTRACT

A protective layer of a refractory material deposited on a metal electrode layer of an oxygen sensing element is improved by a process comprising forming the protective layer onto the surface of the metal electrode layer by plasma spray coating the surface of the metal electrode layer, first with a refractory material powder at a position of a prescribed distance from a plasma spray coating device and at a prescribed electric power, and second, with a refractory material powder having the same particle size and composition as said refractory material powder used in the first plasma spray coating at a position of a distance greater than said prescribed distance and/or at an electric power lower than said prescribed electric power.

6 Claims, 7 Drawing Figures

PROCESS FOR PRODUCING OXYGEN SENSING ELEMENT

BACKGROUND OF THE INVENTION

The invention relates to a process for producing an oxygen sensing element capable of measuring the partial pressure of oxygen in sample gases. More particularly, the invention relates to a process for producing an oxygen sensing element suitable for use in an exhaust gas purifying system wherein the content of oxygen in the exhaust gas from the internal combustion engine of an automobile is measured, thereby to determine the content of unburnt hydrocarbons, carbon monoxide and nitrogen oxides in the exhaust gas and, based on the measurement results, the air-fuel ratio is appropriately adjusted so that the efficiency of a catalyst for purifying the exhaust gas is enhanced.

An oxygen sensor is an oxygen concentration cell having a structure such that electrodes are mounted on the opposite sides of a solid electrolyte composed of a sintered ceramic material capable of conducting an oxygen ion. An electromotive force is produced across the solid electrolyte by the difference in the partial pressure between the oxygen in reference and sample gases contacting opposite sides of the solid electrolyte. The concentration of oxygen in the sample gas can be determined by measuring the electromotive force that is produced. As is well known, such an oxygen sensor is also employed, in combination with an electronic fuel injection device mounted on the internal combustion engine of an automobile or a platinum group catalyst layer provided upstream an exhaust gas flow from the internal combustion engine, to detect the concentration of oxygen in the exhaust gas being under an approximately equilibrium condition.

There has been a problem with conventional oxygen sensors mounted on automobiles, in that phosphorus, lead and the like contained in the exhaust gas penetrate into the oxygen sensing element and fill up the gaps between the solid electrolyte granules causing the lowering of the function of the oxygen sensing element. In order to solve such a problem, it is proposed that a protective layer of a refractory material having pores capable of passing the exhaust gas therethrough is provided on the outer surface of the oxygen sensing element (see, for example, Publicly Disclosed Japanese Patent Application (Kokai) No. 48-90294). The protective layer of this element performs a protective function for a certain period of use. However, when used for an extended period of time, the pores of the protective layer are filled up with phosphorus, lead and the like which lowers the function of the oxygen sensing element. Further, the protective layer may sometimes be peeled from the surface of the element upon use.

Such a protective layer of a refractory material is produced conventionally by dipping an oxygen sensing element provided with a protective layer thereon in a slurry of a metal oxide to coat the surface of the element with the slurry and, then, sintering the coated slurry. Alternatively, the protective layer may be produced by a plasma spray coating technique.

SUMMARY OF THE INVENTION

The primary object of the present invention is to provide a process for producing an oxygen sensing element having an improved protective layer which will eliminate the above-mentioned defects of the protective layers of the conventional oxygen sensing elements.

Other objects and advantages of the present invention will be apparent from the following description.

The present invention provides a process for producing an oxygen sensing element comprising an ion-conducting tubular solid electrolyte member composed of a sintered material and closed at one end, a first metal electrode layer deposited on the inner surface of the solid electrolyte member, a second metal electrode layer deposited on the outer surface of the solid electrolyte member, and a protective layer of a refractory material deposited on the surface of the second metal electrode layer. This process of the present invention comprises forming the protective layer onto the surface of the second metal electrode layer by plasma spray coating the surface of the second electrode layer, first with a refractory material powder at a position of a prescribed distance from a plasma spray coating device and at a prescribed electric power, and then, with a refractory material powder having the same particle size and composition as said refractory material powder used in the first plasma spray coating at a position of a distance greater than said prescribed distance and/or at an electric power lower than said prescribed electric power.

DESCRIPTION OF PREFERRED EMBODIMENTS

An uncoated oxygen sensing element to be employed in the plasma spray coating according to the present invention may have a structure such that a solid electrolyte member composed of a sintered material such as of a $ZrO_2$—CaO mixture is formed into a tubular elongated body closed at one end, wherein air employed as an oxygen-containing gas in reference is introduced into the inside thereof and a sample exhaust gas flows into the outside thereof. On the inner peripheral surface of the tubular solid electrolyte, a porous first electrode such as of platinum is deposited in a thickness of 0.5 to 2 $\mu$m. This porous first electrode may be deposited by plating or the baking of a platinum paste. Likewise, on the outer peripheral surface of the tubular solid electrolyte, a porous second electrode such as of platinum is deposited in a thickness of 0.5 to 2 $\mu$m. These electrodes comprise a portion to produce an electromotive force between it and the air or exhaust gas and a portion to lead the produced electromotive force out of the oxygen sensing element.

Embodiments of the present invention are described below with reference to the accompanying drawings.

Figure 1:
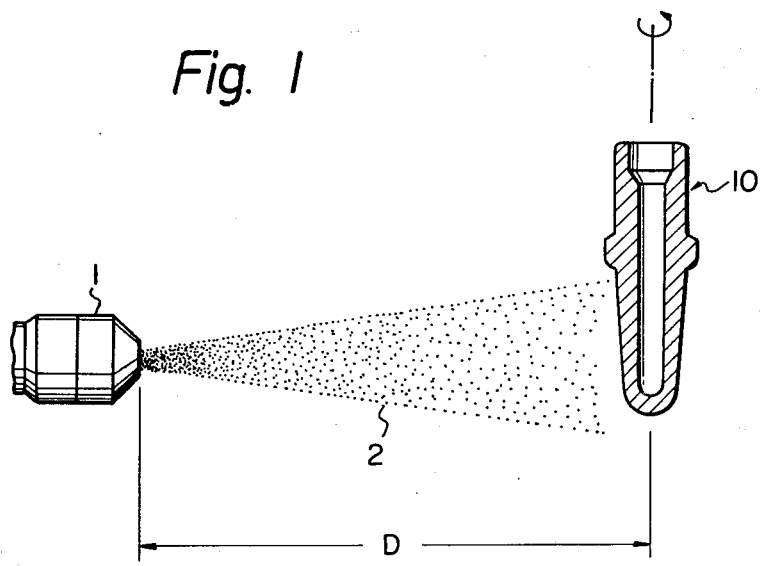
FIG. 1 is a schematic view illustrating a state of a plasma spray coating, wherein the torch portion of a plasma spray coating device and an oxygen sensing element to be coated are illustrated.

Referring now to FIG. 1, a refractory material powder 2 is ejected in a spray form from the torch portion 1 of a plasma spray coating device, such as a plasma spray gun, against the outer surface of an oxygen sensing element 10 having a structure as mentioned above, suspended at a position of a distance D from the torch portion 1. The oxygen sensing element 10 is rotated around its longitudinal axis. In this way, a porous layer of the refractory material is deposited on the outer surface of the oxygen sensing element.

It has now been found that when the distance D between the torch portion of the plasma spray coating device and the suspended oxygen sensing element is increased during the plasma spray coating and the properties of the refractory material powder being ejected remain unchanged, the properties of the refractory material layer being deposited are advantageously changed, and thus, the durability of the resulting oxygen sensing element is greatly increased. Such advantageous change of the deposited refractory material layer may also be attained by decreasing the electric power applied to the plasma spray coating device, instead of, or in conjunction with, the increase of the distance D.

The reasons why the above-mentioned change of the properties of the deposited refractory material layer occurs during the plasma spray coating according to the present invention are not clear at the present time. However, it is supposed that the change in the properties may occur due to the change in the size or shape of the pores in the deposited layer. Or the change in the properties may be produced due to the increase of the bonding strength of the deposited layer to the oxygen sensing element surface.

According to an embodiment of the present invention, it has been found that a preferable refractory protective layer can be obtained, if the spray distance D is increased from 140 mm to 160 mm and/or the electric power is decreased from 33 KW to 20 KW, in the case where a refractory material powder of particle sizes within a range between 30 and 40 μm is employed.

According to another embodiment, it has also been found that the properties of the sequentially deposited two portions of the resulting protective layer are advantageously balanced, where the refractory protective layer is first deposited in 20 to 100 μm thick and second, after changing the spray distance and/or the electric power, deposited in 5 to 100 μm thick. Where, in the resulting protective layer, the first deposited portion has a thickness of 50 to 80 μm and the second deposited portion has a thickness of 40 to 100 μm, particularly excellent durability and response characteristics are achieved in the resulting oxygen sensing element.

Figure 2A:
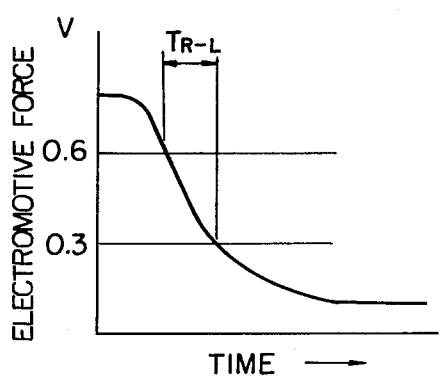
FIGS. 2A and 2B are graphs each showing the response characteristic of an oxygen sensing element.
Figure 2B:
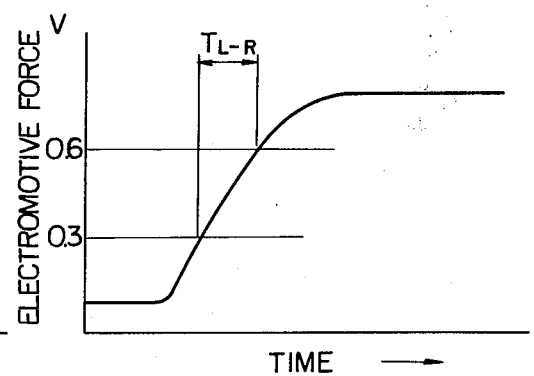

In FIGS. 2A and 2B, the graphs illustrate the response characteristic of an oxygen sensing element upon the change of the oxygen concentration in an exhaust gas. FIG. 2A shows the response that is characteristic in the case where the combustion condition is changed from rich side to lean side with respect to a stoichiometric condition, while FIG. 2B shows the response that is characteristic when the combustion condition is changed from lean side to rich side. The change of the combustion condition causes the decrease or the increase of the electromotive force of an oxygen sensing element with a certain time lag. The response that is characteristic is represented by the response time, i.e. the time $[T_{R-L}]$ required when the electromotive force is changed from 0.6 volt to 0.3 volt or the time $[T_{L-R}]$ required when the electromotive force is changed from 0.3 volt to 0.6 volt. It is inevitable that the response time of an oxygen sensing element becomes prolonged gradually with the use thereof. However, in the oxygen sensing element produced by the process of the present invention, the increase of the response time can be advantageously inhibited, i.e. the durability becomes greatly increased, as hereinafter mentioned.

In the process of the present invention, the plasma spray coating may be carried out in one stage by changing the applied electric power and the spray distance (D) continuously or at a time. Alternatively, the plasma spray coating may be carried out in two stages by interrupting the plasma spray coating for the change of the electric power and the spray distance.

It is advantageous, in view of the practicality of using refractory material, to employ a mixture of nitrogen and hydrogen gases as the gas for generating plasma which also acts as a carrier gas for the refractory material powder. It is suitable, in general, that the gas for generating plasma has a flow rate within a range of 100 to 150 standard cubic feet per hour (SCFH). The refractory materials that are usable for the present invention include $Al_2O_3$, $MgO \cdot Al_2O_3$, a $CaO/ZrO_2$ mixture and a $Y_2O_3/ZrO_2$ mixture, and a mixture of two or more thereof.

In a further embodiment of the present invention, the protective layer of the refractory material may be formed on a platinum group catalyst layer, such as of platinum, rhodium or palladium, deposited on the second electrode layer. Such a catalyst layer may usually be formed into 0.5 to 5 μm thick by electroless plating or the baking of a frit-free paste.

Figure 3:
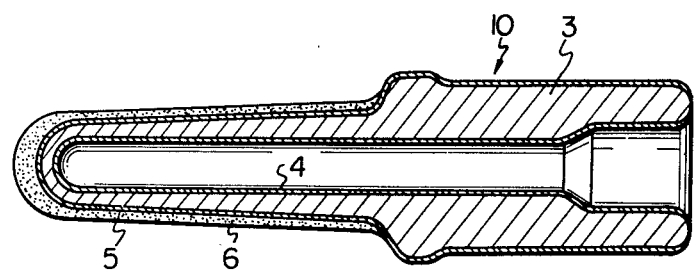
FIG. 3 illustrates a sectional view of an oxygen sensing element.

The present invention will be further illustrated by way of examples, below. In the following examples, oxygen sensing elements as illustrated in FIG. 3 were produced. The tubular solid electrolyte 3 of the illustrated oxygen sensing element 10 is composed of a $ZrO_2/CaO$ solid solution. On the inner surface of the solid electrolyte 3 a porous platinum first electrode 4 of 1 μm thick is deposited and on the outer surface, a porous platinum second electrode 5 of 1 μm thick is deposited. Further, on an area of the surface of the second electrode 5 to be brought into contact with an exhaust gas, a protective layer 6 is deposited.

The plasma spray coating for forming the protective layer 6 was carried out using a plasma spray gun (made by METCO INC.) and employing as a gas for generating plasma a mixture of 13% $H_2$ and 87% $N_2$ at a flow rate of 100 SCFH, and a refractory material powder, a γ-$Al_2O_3$ powder of particle sizes of 5 to 20 μm.

EXAMPLE 1

In this example, the protective layer 6 was formed to a thickness of 120 μm. The plasma spray coating was carried out, first, (1) under the conditions of a voltage of 65 V, a plasma current of 500 A, an electric power of 33 KW, a spray distance (D) of 140 mm and a spray time of 10 sec., and subsequently, (2) under the conditons of a voltage of 65 V, a plasma current of 300 A, an electric power of 20 KW, a spray distance (D) of 140 mm and a spray time of 10 sec. Thus, an oxygen sensing element (type I) was obtained.

For comparison, a comparative oxygen sensing element (type II) was produced in a manner as mentioned above, except that the plasma spray coating was carried out under the conditions of a voltage of 65 V, a plasma current of 500 A, an electric power of 33 KW, a spray distance (D) of 140 mm and a spray time of 20 sec.

Using the oxygen sensing elements produced as above, the response times $T_{R-L}$ and $T_{L-R}$ were measured, respectively, by changing the equivalence ratio $\lambda$ as defined by the formula:

$$\lambda = \frac{\text{actual air/fuel ratio}}{\text{stoichiometric air/fuel ratio}}$$

from 0.9 (rich side) to 1.1 (lean side) and vice versa. For the measurement, each of the oxygen sensing elements was incorporated in an oxygen sensor box in communication with the exhaust manifold of an internal combustion engine operated in a steady state and maintained at a temperature of 500°±5° C. by the exhaust gas. A lubricating oil of high phosphorus content was used for the internal combustion engine.

Figure 4:
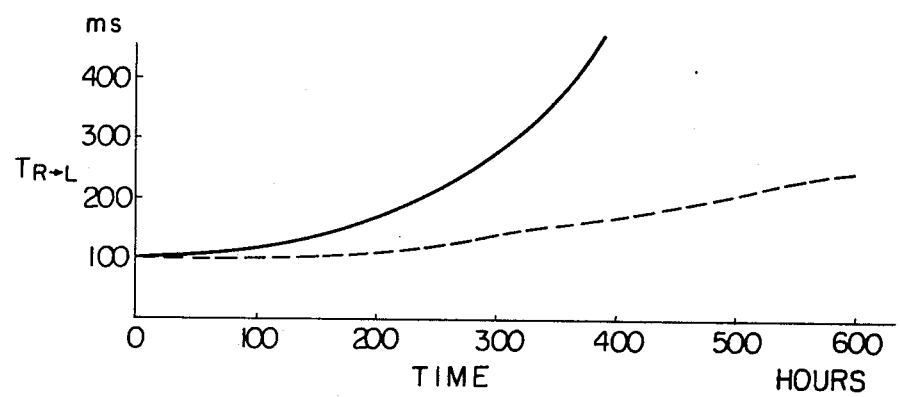
FIGS. 4 and 5 are graphs showing the change of response time with the lapse of time of oxygen sensing elements.
Figure 5:
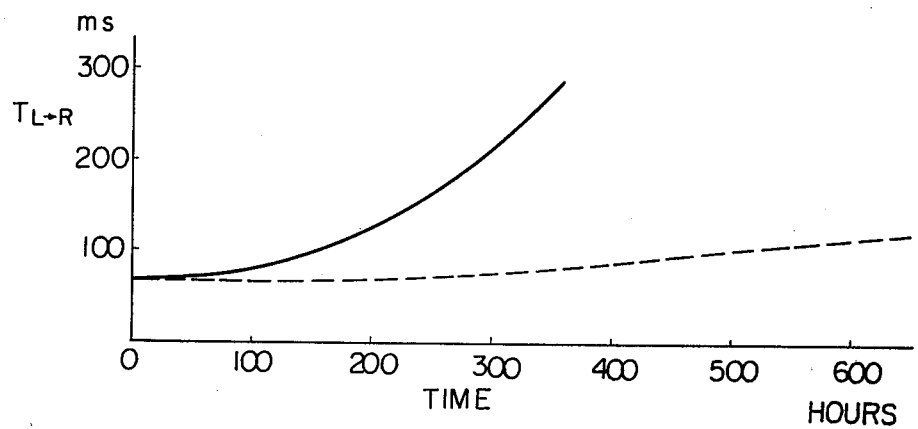

FIGS. 4 and 5 show the respective changes of $T_{R-L}$ and $T_{L-R}$ with time. In the figures, the dotted lines show the changes in the oxygen sensing element (type I) and the solid lines show the changes in the comparative oxygen sensing element (type II). From these figures, it is proved that the response characteristic of the oxygen sensing element produced according to the process of the present invention is very durable in an exhaust gas of high phosphorus content.

EXAMPLE 2

The procedure as in Example 1 employed for obtaining the oxygen sensing element (type I) was repeated, except that in the conditions (2), the electric power was 33 KW instead of 20 KW and the spray distance (D) was 160 mm instead of 140 mm. The response characteristic of the obtained oxygen sensing element was approximately identical to the oxygen sensing element (type I) of Example 1.

EXAMPLE 3

Oxygen sensing elements (type I) and comparative oxygen sensing elements (type II) obtained as in Example 1 were subjected to a peeling test. Each of the elements was exposed to a temperature of 800° C. in the exhaust manifold of an internal combustion engine operated at an air/fuel ratio of 13. This procedure was repeated for plurality of the respective elements (type I and type II) and the peeling percentage was calculated by dividing the number of the elements, the protective layer of which was peeled by a knife edge, with the number of the tested elements.

Figure 6:
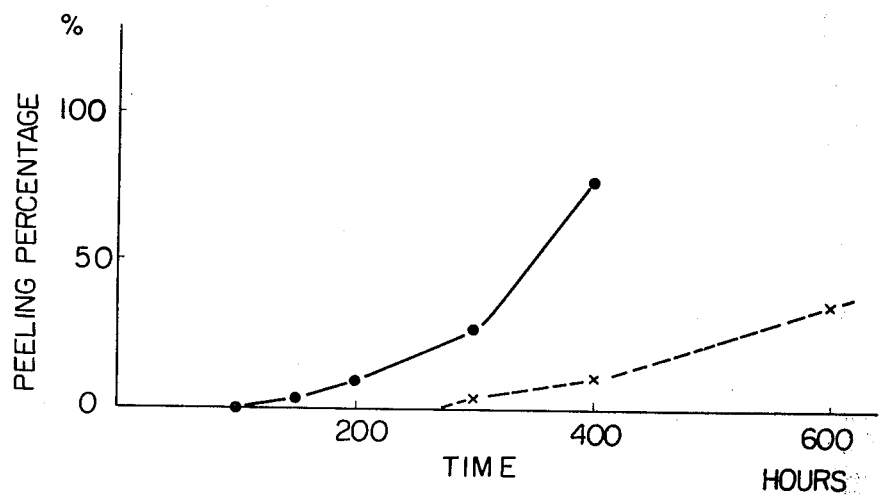
FIG. 6 is a graph showing the change of peeling percentage with the lapse of time of oxygen sensing elements.

The results are shown in FIG. 6. In the figure, the dotted line shows the peeling percentage obtained for the oxygen sensing elements (type I) and the solid line shows the peeling percentage for the oxygen sensing elements (type II). From the figure, it is proved that the oxygen sensing element produced according to the process of the present invention has an excellent peeling resistance.

What is claimed is:

1. A process for producing an oxygen sensing element suitable for use in a combustion exhaust gas purifying system comprising an ion-conducting tubular solid electrolyte member composed of a sintered material and closed at one end, a first metal electrode layer deposited on the inner surface of the solid electrolyte member, a second metal electrode layer deposited on the outer surface of the solid electrolyte member, and a protective layer of a refractory material deposited on the surface of the second metal electrode layer, which process comprises forming the protective layer onto the surface of the second metal electrode layer by plasma spray coating the surface of the second electrode layer, first with a refractory material powder from a plasma spray coating device, and at a position of a prescribed distance from a plasma spray coating device and at a prescribed electric power, said distance and power being such that a durable protective layer is formed, and second with a refractory material powder having the same particle size and composition as said refractory material powder used in the first plasma spray coating at a position of a distance greater than said prescribed distance and/or at an electric power lower than said prescribed electric power.

2. A process according to claim 1, wherein the refractory protective layer is deposited first in 20 to 100 μm thick and second, after changing said distance and/or said electric power, in 5 to 100 μm thick.

3. A process according to claim 1, wherein the plasma spray coating is carried out in one stage.

4. A process according to claim 1, wherein the refractory material comprises at least one member selected from the group consisting of $Al_2O_3$, $MgO.Al_2O_3$, a $CaO/ZrO_2$ mixture and a $Y_2O_3/ZrO_2$ mixture.

5. A process according to claim 1, wherein a refractory material powder of particle sizes within the range of between 30 μm and 40 μm is employed, and said distance is increased from 140 mm to 160 mm and/or the electric power is decreased from 33 kw to 20 kw.

6. A process for producing an oxygen sensing element suitable for use in a combustion exhaust gas purifying system, comprising an ion-conducting tubular solid electrolyte member composed of a sintered material and closed at one end, a first metal electrode layer deposited on the inner surface of the solid electrolyte member, a second metal electrode layer deposited on the outer surface of the solid electrolyte member, and a protective layer of a refractory material deposited on the surface of the second metal electrode layer, which process comprises forming the protective layer onto the surface of the second metal electrode layer, first with a refractory material at a position of a prescribed distance from a plasma spray coating device and at a prescribed electric power, said distance and power being such that a durable protective layer is formed, and second, with a refractory material powder having the same particle size and composition as said refractory material powder used in the first plasma spray coating at a position of a distance greater than said prescribed distance and/or at an electric power lower than said prescribed electric power such that said particle size and composition of said refractory material powder, and the increase in said distance, and/or the decrease in said electric power, are selected such that the peel strength of said protective layer, and the durability of said oxygen sensing element are greater than the peel strength and durability of conventional oxygen sensing elements prepared by spray coating at substantially constant distance and constant electric power.

* * * * *